United States Patent [19]

Haase

[11] Patent Number: 4,555,015

[45] Date of Patent: Nov. 26, 1985

[54] ANIMAL REPELLENT BAG PACKAGE AND METHOD OF PREPARING THE SAME

[75] Inventor: Donald A. Haase, Fairport, N.Y.

[73] Assignee: Mobil Oil Corporation, New York, N.Y.

[21] Appl. No.: 484,763

[22] Filed: Apr. 14, 1983

[51] Int. Cl.$^4$ ............................................... B65D 85/84
[52] U.S. Cl. ................................... 206/0.5; 206/524.4; 206/524.5
[58] Field of Search ................... 206/524.4, 524.5, 0.5, 206/554; 239/55

[56] References Cited

U.S. PATENT DOCUMENTS 4,202,472  5/1980  Lin ........................................ 383/40
4,349,123  9/1982  Yang .................................... 206/554

FOREIGN PATENT DOCUMENTS 56-65803  6/1981  Japan .

Primary Examiner—Joseph Man-Fu Moy
Attorney, Agent, or Firm—Alexander J. McKillop; Michael G. Gilman; Charles J. Speciale

[57] ABSTRACT

A package of a plurality of plastic film bags, said bags having over comparatively broad surfaces of both the inside and outside of said bags, an effective proportion of an animal repellent comprising methyl nonyl ketone, said repellent having emanated from a comparatively small area of said film while said bags were in the folded condition within said package, said package being sealed and the walls thereof being impervious to said animal repellent and a method of forming the same.

3 Claims, No Drawings

ANIMAL REPELLENT BAG PACKAGE AND METHOD OF PREPARING THE SAME

BACKGROUND OF THE INVENTION

This invention is generally concerned with animal repellent bags, animal repellent bag packages and methods of preparing the same.

In recent years it has become common practice to confine household and restaurant garbage in plastic bags. Such plastic bags, even when securely closed, are subject to being ravaged by domestic animals, such as, dogs and cats, and the contents strewn about before an opportunity is had to remove them to a landfill. Chemical agents are sometimes employed to discourage such animals from approaching garbage receptacle areas. Particularly effective animal repellent agents are disclosed in U.S. Pat. No. 4,169,898, issued Oct. 2, 1979, the contents of which are incorporated herein by reference in its entirety. This patent teaches that methyl nonyl ketone and cinnamaldehyde are useful animal repellents. The patent also teaches that a combination of the two materials is an even more effective animal repellent. The aforementioned patent teaches that the repellent combination can be effectively applied to metal or plastic garbage cans, plastic bags, paper and cardboard boxes and the like by means of a spray applicator of the pump type, or an aerosol-type spray can containing, in addition to the repellent agents and a suitable carrier, a conventional self-propellant composition. It is taught that the application be directly to the outside of the container or to the area immediately surrounding the container or even blended with the structure of the container itself during manufacture, e.g. the so-called disposable plastic garbage bags.

It is an object of the present invention to provide a convenient means for repelling domestic animals from refuse and garbage areas.

SUMMARY OF THE INVENTION

The present invention is concerned with a method of preparing an animal repellent plastic bag comprising:

applying to a comparatively small area of the inside surface of a plastic bag, an effective proportion of an animal repellent comprising methyl nonyl ketone, folding said bag upon iself at least once and permitting said repellent to migrate over comparatively large areas inside and outside of said bag.

In a preferred method, the repellent is a combination of cinnamaldehyde and methyl nonyl ketone.

The present invention also provides a method of forming a package of animal repellent plastic bags comprising:

(a) applying to a plastic film surface an effective proportion of an animal repellent comprising methyl nonyl ketone;

(b) forming a plurality of individual bags from said plastic film;

(c) folding each bag upon itself at least once; and (d) enclosing a plurality of the thus folded bags in a package, the walls of which are at least substantially impervious to said repellent. As above noted, the preferred repellent is a combination of cinnamaldehyde and methyl nonyl ketone.

The present invention also provides for a continuous method of forming packages of plastic bags comprising, feeding plastic film to automatic bag-making means to form a plurality of bags, folding said bags and inserting a plurality of bags into packages, wherein the improvement comprises: applying an effective proportion of an animal repellent comprising methyl nonyl ketone to small areas of either side of said film and sealing said plurality of bags into said packages, the walls of which are at least substantially impervious to said repellent.

DESCRIPTION OF THE PREFERRED EMBODIMENTS

By the present invention it has been discovered that the animal repellent, methyl nonyl ketone, has the ability on being applied to a comparatively small surface area of a plastic to migrate to a comparatively large area of a plastic surface even to the extent of migrating to the opposite surface of a plastic film. When such a film is converted into the form of a plastic bag, for example, a 30 gallon trash bag, and a small proportion, for example, 0.1 gram of methyl nonyl ketone is applied to a small area on the inside surface of the bag, then after the bag is folded up the methyl nonyl ketone will, after the passage of time, be found on both surfaces of the plastic film and over a large area of both sides thereof. It is not fully understood whether the methyl nonyl ketone moves to both sides of the film because of extensive creep or via solution transport through certain polymers or through molecular voids in the plastic film. The methyl nonyl ketone also has been found to be effective in carrying with it another known animal repellent, i.e. cinnamaldehyde. Thus, the synergistic combination of the methyl nonyl ketone and cinnamaldehyde disclosed in U.S. Pat. No. 4,169,898 supra is a preferred repellent composition for the instant invention. No vehicle is necessary for the effective transport of the animal repellent composition of the present invention.

By the present invention, it is to be undersstood that the animal repellent can be methyl nonyl ketone alone or in combination with cinnamaldehyde. When employed in combination with cinnamaldlehyde, it can be employed in a ratio of from 1 to 4 parts by weight methyl nonyl ketone to from 1 to 4 parts by weight cinnamaldehyde. The amount of the animal repellent need only be an amount effective to repel or discourage an animal from attacking or tearing open the subject bags. A preferred amount of animal repellent for a bag in the size range of from about 5 to 50 gallons capacity is from about 0.01 to about 1 gram per bag. Particularly preferred is a range of from about 0.05 to about 0.3 grams. While any thickness filmcan be employed in forming the bags of the present invention, it is preferred that the film thickness range from about 0.5 to about 4 mils. A particularly preferred range is from about 0.75 to about 2 mils.

A general method of preparing the treated bags contemplated by the present invention involves the use of commercially available automatic equipment. State of the art apparatus continuously extrudes a bubble or tube of molten polyethylene from a die and at a downstream location the bubble is collapsed and slit through the center so as to form two continuous C or U-shaped films. At this point an applicator applies approximately 0.10 gram per bag of a mixture containing 80% by weight cinnamaldehyde and 20% by weight methyl nonyl ketone to what will be the inside surface of each bag. Thereafter, individual bags are formed by heat sealing and severing the continuous U-shaped segments of the extruded tube to form individual bags. These bags are then automatically folded a plurality of times and 50 bags are sealed within an aluminum foil-polyethylene film laminate pouch and sealed closed.

It has been determined that trash bags, so treated and sealed within a pouch, will become pervaded by the animal repellent inside and outside thereof over all or substantially all of the surfaces of the film of the bags. The spreading or pervading of the repellent begins immediately after the pouch is sealed and is effectively present over the surfaces within a few days. By the time the package arrives on a store shelf, usually not less than two weeks from the time of packaging, effective coverage inside and outside of the trash bags is well accomplished.

EXAMPLE

50 Hefty ® brand polyethylene trash can liners of the 30 gallon size, were treated with 0.10 grams per bag of a mixture containing 80% by weight cinnamaldehyde and 20% by weight methyl nonyl ketone. The bags were 30 inches wide by 36 inches long with a thickness of 1.5 mils and a weight of about 50.0 grams per bag. The active ingredients constituted about 0.2% of the bag weight. These bags were folded and sealed within an aluminum-polyethylene laminate film pouch.

While any plastic film material can be employed in the manufacture of the trash bags contemplated herein polyolefin films are preferred. Particularly preferred among the polyolefin films is polyethylene films. As employed herein the term polyethylene is employed somewhat in a generic sense to include polyethylene films per se, both high density and low density polyethylene, linear low density polyethylene copolymerized with an alpha olefin, e.g. propylene butene-1, etc., polyethylene blended with polypropylene, polyethylene laminated or coextruded with another thermoplastic film and any combinations of the foregoing.

The experimental data set forth hereinbelow shows the results of applying the subject repellent to the interior surface of the plastic trash bags which were then folded a plurality of times and sealed within the aluminum-polyethylene pouch for a period of from 30 to 60 days versus untreated bags.

The definition of the degree of damage done to the bags by the dogs is as follows:
None—No marks on bags
Slight—Small tear but no loss of contents
Moderate—Moderate tear but limited loss of contents
Severe—Destroyed bag, scattered contents.

At the beginning of the test, polyethylene bags filled with crushed newspaper only were placed in pens with individual test dogs who had not been fed for 24 hours. The dogs were allowed one hour to attack the bag. All dogs which attacked the test bags severely were used in subsequent tests. This test is identified below as the "screening test". Thereafter, dogs who had attacked newspaper filled bags severely were employed in further tests. In these tests, a half of a 15 oz. can of mackerel was included with the crushed newspapers. The first set of tests monitored the degree of attack of the dogs against newspaper-mackerel filled-untreated bags vis-a-vis newspaper-mackerel filled-treated bags which bags had been exposed to air for twenty hours. Thereafter, a second set of tests were carried out. Dogs were employed with 20 untreated bags filled with newspapers-mackerel vis-a-vis dogs with 20 treated bags filled with newspapers-mackerel. In this case, the treated bags had been exposed to air for 72 hours. In both sets of tests the cinnamon odor of the bags was not perceptible to humans.

| Bag Series | Total Bags | None | Slight | Moderate | Severe |
|---|---|---|---|---|---|
| Screening-Test | | | | | |
| Newspaper - untreated bags | 118 | 72 | 2 | 13 | 29 |
| Newspaper-mackeral untreated bags | 30 | 7 | 2 | 8 | 13 |
| Newspaper-mackeral treated bags | 30 | 22 | 4 | 5 | 1 |
| Newspaper-mackeral untreated bags | 20 | 4 | 2 | 4 | 10 |
| Newspaper-mackeral treated bags | 20 | 13 | 3 | 2 | 1 |

The foregoing test data shows that the active components of the repellent composition effectively is available at the surfaces of the film of the trash bags so as to repel dogs. The repellent is similarly effective for cats.

What is claimed is:

1. Package containing a plurality of folded bags, comprising a sealed package containing therein a plurality of folded bags, each of said bags having, over comparatively broad surfaces of both the inside and outside thereof, an effective proportion of an animal repellent comprising methyl nonyl ketone which emanates from a comparatively small area of at least one surface of said bag, said small area containing an unconfined amount of said repellent which is applied thereto prior to introduction of said bag into said package to permit said emanation, said emanation occurring during the time said bag is folded and within said sealed package, said sealed package having walls defining said package which are impervious to said repellent.

2. The package of claim 1 wherein said repellent is a mixture of cinnamaldehyde and methyl nonyl ketone.

3. The package of claim 2, wherein said bags are formed of a polyethylene film and said package walls comprise a metal foil.

* * * * *